US006462060B2

(12) United States Patent
Chong et al.

(10) Patent No.: US 6,462,060 B2
(45) Date of Patent: Oct. 8, 2002

(54) HETEROCYCLIC-HYDROXYIMINO-FLUORENE NUCLEI COMPOUNDS AND PHARMACEUTICAL COMPOSITIONS FOR INHIBITING PROTEIN KINASES, AND METHODS FOR THEIR USE

(75) Inventors: Wesley Kwon Mung Chong, Encinitas; Rohit Kumar Duvadie, San Diego, both of CA (US)

(73) Assignee: Agouron Pharmaceuticals, Inc., La Jolla, CA (US)

( * ) Notice: Subject to any disclaimer, the term of this patent is extended or adjusted under 35 U.S.C. 154(b) by 0 days.

(21) Appl. No.: 09/930,255

(22) Filed: Aug. 16, 2001

(65) Prior Publication Data

US 2002/0049238 A1 Apr. 25, 2002

Related U.S. Application Data

(60) Provisional application No. 60/224,805, filed on Aug. 18, 2000.

(51) Int. Cl.$^7$ .................. C07D 285/14; A61K 31/381; A61K 31/4192; A61K 31/4245; A61K 31/4184

(52) U.S. Cl. .................. 514/362; 514/364; 514/385; 514/359; 548/127; 548/257; 548/259; 548/260; 548/301.7

(58) Field of Search .................. 548/301.7, 257, 548/126, 127, 259, 260; 514/385, 359, 364, 362

(56) References Cited

U.S. PATENT DOCUMENTS

| 5,621,082 A | 4/1997 | Xiong et al. ............ 530/350 |
| 5,733,920 A | 3/1998 | Mansuri et al. .......... 514/337 |
| 6,316,603 B1 * | 11/2001 | McTigue et al. .......... 530/402 |

FOREIGN PATENT DOCUMENTS

| EP | 0666270 A2 | 9/1995 |
| WO | WO96/14843 | 5/1996 |
| WO | WO97/16447 | 9/1997 |
| WO | WO97/34876 | 9/1997 |
| WO | WO97/42949 | 11/1997 |
| WO | WO97/45397 | 12/1997 |
| WO | WO98/17662 | 4/1998 |
| WO | WO98/33798 | 8/1998 |
| WO | WO99/02162 | 1/1999 |
| WO | WO99/15500 | 4/1999 |
| WO | WO99/17769 | 4/1999 |
| WO | WO99/21845 | 5/1999 |
| WO | WO99/30710 | 6/1999 |
| WO | WO99/43675 | 9/1999 |
| WO | WO99/43676 | 9/1999 |
| WO | WO99/54308 | 10/1999 |
| WO | WO99/62890 | 12/1999 |
| WO | WO00/12485 | 3/2000 |
| WO | WO00/12486 | 3/2000 |
| WO | WO 00/27822 | 5/2000 |

OTHER PUBLICATIONS

Adams et al., *Curr. Opin. Drug Disc. Dev.* 2, 96–109 (1999).
Al–Khodairy et al., *Molec. Biol. Cell* 5, 147–160 (1994).
*Ann. Rev. Cell Dev. Biol.* 13, 261–291 (1997).
Bagshawe, *Drug Dev. Res.* 34, 220–230 (1995).
Bandara et al., *Nature Biotechnology*, 15, 896–901 (1997).
Bertolini et al., *J. Med. Chem.* 40, 2011–2016 (1997).
Bodor, *Advances in Drug Res*, 13, 255–331 (1984).
Bolen, *Oncogene* 8, 2025–2031 (1993).
Bundgaard, *Design of Prodrugs*, (Elsevier Press) (1985).
Bunz et al., *Science* 282, 1497–1501 (1998).
Carr, *Science* 287, 1765–1766 (2000).
Chang et al., *Chemistry & Biology* 6, 361–375 (1999).
Chen et al., *Cell* 100, 681–692 (2000).
Chen et al., *Proc. Natl. Acad. Sci.* USA 96, 4325–4329 (1999).
Klohs et al., *Curr. Op. Chem. Biol.* 10, 544–549 (1999).
Cohen et al., *Proc. Natl. Acad. Sci.* USA 95, 14272–14277 (1998).
Del Sal et al., *Critical Rev. Oncogenesis* 7(1&2), 127–142 (1996).
Eckert et al., *Journal für Praktische Chemie* 118, 263–281 (1928).
El–Deiry et al., *Cell* 75, 817–825 (1993).
Folkman, *Nature Med.* 1, 27–31 (1995).
Garcia–Echeverria et al., *Med. Res. Rev.* 20, 28–57 (2000).
Grant et al., *Proc. Amer. Assoc. Cancer Res.* 39, Abst. 1207 (1998).
Gray et al., *Curr. Med. Chem.* 6, 859–875 (1999).
Gray et al., *Science* 281, 533–538 (1998).
Hall et al., *Adv. Cancer Res.* 68, 67–108 (1996).
Harper, *Cancer Surv.* 29, 91–107 (1997).
Hartwell et al., *Science* 266, 1821–1828 (1994).
Hartwell et al., *Science* 246, 629–634 (1989).
Hirao et al., *Science* 287, 1824–1827 (2000).
Holash et al., *Oncogene* 18, 5356–5362 (1999).
Jeffrey et al., *Nature* 376, 313–320 (1995).
Kamb et al., *Science* 264, 436–440 (1994).
Kamb, *Trends in Genetics* 11, 136–140 (1995).

(List continued on next page.)

*Primary Examiner*—Joseph K. McKane
*Assistant Examiner*—Rebecca Anderson
(74) *Attorney, Agent, or Firm*—Shanks & Herbert

(57) ABSTRACT

Compounds with heterocyclic-hydroxyimino-fluorene nuclei that modulate and/or inhibit the activity of certain protein kinases are described. These compounds and pharmaceutical compositions containing them are capable of mediating tyrosine kinase signal transduction in order to modulate and/or inhibit unwanted cell proliferation. The invention is also directed to the therapeutic or prophylactic use of pharmaceutical compositions containing such compounds, and to methods of treating cancer as well as other disease states associated with unwanted angiogenesis and/or cellular proliferation, such as diabetic retinopathy, glaucoma, rheumatoid arthritis, and psoriasis, by administering effective amounts of such compounds.

12 Claims, No Drawings

OTHER PUBLICATIONS

Krosgaard–Larsen et al., eds., Drug Design and Development, *Design and Application of Prodrugs,* Harwood Academic Publishers, (1991).
Kunick et al., *Bioorg. Med. Chem. Lett.* 10, 567–569 (2000).
Lee et al., *Biochemistry* 23, 4255–4261 (1984).
Legraverend et al., *Bioorg. Med. Chem. Lett.* 8, 793–798 (1998).
Legraverend et al., *J. Med. Chem.* 43, 1282–1292 (2000).
Loda et al., *Nature Medicine* 3, 231–234 (1997).
Luzzio et al., *Proc. Amer. Assoc. Cancer Res.,* Abst. 4102 (1999).
Maisonpierre et al., *Science* 277, 55–60 (1997).
Marhevka et al., *J, Med. Chem.* 28, 18–24 (1985).
Matsuoka, *Science* 282, 1893–1897 (1998).
Matsumoto et al., *Chem. Pharm. Bull* 47, 971–979 (1999).
McMahon et al., *Curr. Opin. Drug. Disc. Dev.* 1, 131–146 (1998).
McMahon et al., *Oncologist,* 5, 3–10 (2000).
McTigue et al., *Structure* 7, 319–330 (1999).
Merenmies et al., *Cell Growth & Differentiation* 8, 3–10 (1997).
Meyer et al., *Proc. Amer. Assoc. Cancer Res.* 39, Abst. 3794 (1998).
Millauer et al., *Cancer Research* 56, 1615–1620 (1996).
Mohammadi et al., *EMBO Journal* 17, 5896–5904 (1998).
Mossman, *Journal of Immunological Methods* 65, 55–63 (1983).
Nobori et al., *Nature* 368, 753–756 (1994).
Nurse, *Cell* 91, 865–867 (1997).
Owa et al., *J. Med. Chem.* 42, 3789–3799 (1999).
O'Connor, *Cancer Surveys* 29, 151–182 (1997).
Pan et al., *Chem. & Ind.,* 240–241 (1969).
Parast et al., *Biochemistry* 37, 16788–16801 (1998).
Peng et al., *Science* 277, 1501–1505 (1997).
Perera et al., *J. Chem. Soc. C,* 1348–1354 (1971).
Rosania et al., *Exp. Opin. Ther. Patents* 10, 215–230 (2000).
Rosenblatt et al., *J. Mol. Biol.* 230, 1317–1319 (1993).
Ruetz et al., *Proc. Amer. Assoc. Cancer Res.* 39, Abst. 3796 (1998).
Sanchez et al., *Science* 277, 1497–1501 (1997).
Schow et al., *Bioorg. Med. Chem. Lett.* 7, 2697–2702 (1997).
*Science* 274, 1643–1677 (1996).
Schultz et al., *J. Med. Chem.,* 2909–2919 (1999).
Sedlacek et al., *Int. J. Oncol.* 9, 1143–1168 (1996).
Shan et al., *J. Pharm. Sci.* 7, 765–767 (1997).
Sherr, et al., *Genes Dev.* 13, 1501–1512 (1999).
Sielecki et al., *J. Med. Chem.* 43, 1–18 (2000).
Stadler et al., *J. Clin. Oncol.* 18, 371–375 (2000).
Still et al., *J. Org. Chem.* 43, 2923–2925 (1978).
Stover et al., *Current Opinion in Drug Discovery and Development* 2, 274–285 (1999).
Strawn et al., *Cancer Research* 56, 3540–3545 (1996).
Strawn et al., *Exp. Opin. Invest. Drugs* 7, 553–573 (1998).
Suganuma et al., *Cancer Res.* 59, 5887–5891 (1999).
Thompson, *Oncogene* 15, 3025–3035 (1997).
Toledo et al., *Curr. Med. Chem.* 6, 775–805 (1999).
Walworth et al., *Nature* 363, 368–371 (1993).
Webster, *Exp. Opin. Invest. Drugs* 7, 865–887 (1998).
Weinert, *Science* 277, 1450–1451 (1997).
Winters et al., *Oncogene* 17, 673–684 (1998).
Yoshiji et al., *Cancer Research* 57, 3924–3928 (1997).
Zeng et al., *Nature* 395, 507–510 (1998).
Thomas et al., *J. Biol. Chem.,* 274, 36684–36692 (1999).

* cited by examiner

HETEROCYCLIC-HYDROXYIMINO-FLUORENE NUCLEI COMPOUNDS AND PHARMACEUTICAL COMPOSITIONS FOR INHIBITING PROTEIN KINASES, AND METHODS FOR THEIR USE

RELATED APPLICATION DATA

This application claims priority to U.S. Provisional Patent Application Serial No. 60/224,805, filed Aug. 18, 2000.

FIELD OF THE INVENTION

This invention is directed to compounds with heterocyclic-hydroxyimino-fluorene nuclei that mediate and/or inhibit the activity of certain protein kinases, and to pharmaceutical compositions containing such compounds. The invention is also directed to the therapeutic or prophylactic use of such compounds and compositions, and to methods of treating cancer, as well as other disease states associated with unwanted angiogenesis and/or cellular proliferation, by administering effective amounts of such compounds.

BACKGROUND OF THE INVENTION

Protein kinases are a family of enzymes that catalyze phosphorylation of the hydroxyl group of specific tyrosine, serine, or threonine residues in proteins. Typically, such phosphorylation dramatically alters the function of the protein, and thus protein kinases are pivotal in the regulation of a wide variety of cellular processes, including metabolism, cell proliferation, cell differentiation, and cell survival. Of the many different cellular functions in which the activity of protein kinases is known to be required, some processes represent attractive targets for therapeutic intervention for certain disease states. Two examples are cell-cycle control and angiogenesis, in which protein kinases play a pivotal role; these processes are essential for the growth of solid tumors as well as for other diseases.

Uncontrolled cell proliferation is the insignia of cancer. Cell proliferation in response to various stimuli is manifested by a de-regulation of the cell division cycle, the process by which cells multiply and divide. Tumor cells typically have damage to the genes that directly or indirectly regulate progression through the cell-division cycle.

Cyclin-dependent kinases (CDKs) are serine-threonine protein kinases that play critical roles in regulating the transitions between different phases of the cell-cycle, such as the progression from a quiescent stage in $G_1$ (the gap between mitosis and the onset of DNA replication for a new round of cell division) to S (the period of active DNA synthesis), or the progression from $G_2$ to M phase, in which active mitosis and cell-division occurs. See, e.g., the articles compiled in *Science*, 274, 1643–1677 (1996); and *Ann. Rev. Cell Dev. Biol.*, 13, 261–291 (1997). CDK complexes are formed through association of a regulatory cyclin subunit (e.g., cyclin A, B1, B2, D1, D2, D3, and E) and a catalytic kinase subunit (e.g., cdc2 (CDK1), CDK2, CDK4, CDK5, and CDK6). As the name implies, the CDKs display an absolute dependence on the cyclin subunit in order to phosphorylate their target substrates, and different kinase/cyclin pairs function to regulate progression through specific phases of the cell-cycle.

The progression from $G_1$ to S phase, accomplished by the action of CDK4/cyclin D and CDK2/cyclin E, is subject to a variety of growth regulatory mechanisms, both negative and positive. Growth stimuli, such as mitogens, cause increased synthesis of cyclin D1 and thus increased functional CDK4. By contrast, cell growth can be down regulated in response to DNA damage or negative growth stimuli, by the induction of endogenous inhibitory proteins. These naturally occurring protein inhibitors include $p21^{WAF1/CIP1}$, $p27^{KIP1}$, and the $p16^{INK4}$ family, the latter of which inhibit CDK4 exclusively (see Harper, *Cancer Surv.*, 29, 91–107 (1997). Aberrations in this control system, particularly those that affect the function of CDK4 and CDK2, have been implicated in the advancement of cells to the highly proliferative state characteristic of malignancies, particularly familial melanomas, esophageal carcinomas, and pancreatic cancers. See, e.g., Hall et al., *Adv. Cancer Res.*, 68, 67–108 (1996); Kamb, *Trends in Genetics*, 11, 136–140 (1995); Kamb et al., *Science*, 264, 436–440 (1994).

Over-expression of cyclin D1 is linked to esophageal, breast, and squamous cell carcinomas (see, e.g., DelSal et al., *Critical Rev. Oncogenesis*, 71, 127–142 (1996)). Genes encoding the CDK4-specific inhibitors of the p16 family frequently have deletions and mutations in familial melanoma, gliomas, leukemias, sarcomas, and pancreatic, non-small cell lung, and head and neck carcinomas (see Nobori et al., *Nature*, 368, 753–756 (1994)). Amplification and/or overexpression of cyclin E has also been observed in a wide variety of solid tumors, and elevated cyclin E levels have been correlated with poor prognosis. In addition, the cellular levels of the CDK inhibitor p27, which acts as both a substrate and inhibitor of CDK2/cyclin E, are abnormally low in breast, colon, and prostate cancers, and the expression levels of p27 are inversely correlated with the stage of disease (see Loda et al., *Nature Medicine*, 3, 231–234 (1997)). Recently there is evidence that CDK4/cyclin D might sequester p27, as reviewed in Sherr et al., *Genes Dev.*, 13, 1501–1512 (1999). The p21 proteins also appear to transmit the p53 tumor-suppression signal to the CDKs (see El-Deiry et al., *Cell*, 75, 817–825 (1993)); thus, the mutation of p53 in approximately 50% of all human cancers may indirectly result in deregulation of CDK activity.

The use of compounds as anti-proliferative therapeutic agents that inhibit protein kinase activity is the subject of several patents and publications. For example, WIPO International Publication No. WO 97/45397 discloses certain alkyloxyamino-substituted fluorenones that control protein kinase C activity (e.g., CDC2 kinase activity) in mammals. WIPO International Publication No. WO 99/21845 discloses 4-aminothiazoles as CDK inhibitors. Isothiazole derivatives useful as anticancer agents are disclosed in WIPO International Publication No. WO 99/62890. U.S. Pat. No. 5,621,082 to Xiong et al. discloses nucleic acid derivatives that encode inhibitors of CDK6. Peptides and peptidomimetic inhibitors, including substrate site antagonists, are described in European Patent Publication No. 0 666 270 A2, Bandara et al., *Nature Biotechnology*, 15, 896–901 (1997), and Chen et al., *Proc. Natl. Acad. Sci., USA*, 96, 4325–4329 (1999). Peptide aptamers are identified in Cohen et al., *Proc. Natl. Acad. Sci., U.S A.*, 95, 14272–14277 (1998). Other small molecules have been identified as CDK inhibitors (for recent reviews, see Webster, *Exp. Opin. Invest. Drugs*, 7, 865–887 (1998), Stover et al., *Current Opinion in Drug Discovery and Development*, 2, 274–285 (1999), and Rosania et al., *Exp. Opin. Ther. Patents*, 10, 215–230 (2000)). The flavone flavopiridol, displays modest selectivity for inhibition of CDKs over other kinases, but inhibits CDK4, CDK2, and CDK1 equipotently, with $IC_{50}$s in the 0.1–0.3 µM range. Flavopiridol is currently in Phase II clinical trials as an oncology chemotherapeutic (Stadler et al., *J. Clin. Oncol.*, 18, 371–375 (2000) and Sedlacek et al., *Int. J. Oncol.*, 9, 1143–1168 (1996)). Analogs of flavopiridol are the subject of other publications, for example, U.S. Pat. No. 5,733,920 to Mansuri et al. (WIPO International Publication No. WO 97/16447) and WIPO International Publication Nos. WO 97/42949, and WO 98/17662. Results of inhibition of CDKs with purine-based derivatives are described in Schow et al., *Bioorg. Med. Chem. Lett.*, 7, 2697–2702 (1997); Grant et al., *Proc. Amer. Assoc. Cancer Res,*. 39, Abst. 1207 (1998); Legraverend et al., *Bioorg. Med. Chem. Lett.*, 8, 793–798 (1998); Legraverend et al., *J. Med. Chem.*, 43, 1282–1292 (2000); Gray et al., *Science*, 281, 533–538 (1998); Chang et al., *Chemistry & Biology*, 6, 361–375 (1999); and WIPO International Publication Nos. WO 99/02162, WO 99/43675, and WO 99/43676.

In addition, the following publications disclose certain pyrimidines that inhibit cyclin dependent kinases and growth-factor mediated kinases: WIPO International Publication Nos. WO 00/12485, WO 00/12486, and WO 98/33798; Ruetz et al., *Proc. Amer. Assoc. Cancer Res.*, 39, Abst. 3796 (1998); and Meyer et al., *Proc. Amer. Assoc. Cancer Res.*, 39, Abst. 3794 (1998). Benzensulfonamides that block cells in G1 are in development by Eisai, see Owa et al., *J. Med. Chem.*, 42, 3789–3799 (1999). An oxindole CDK inhibitor is in development by Glaxo-Wellcome, see Luzzio et al., *Proc. Amer. Assoc. Cancer Res.*, Abst. 4102 (1999) and WIPO International Publication No. WO 99/15500. Paullones were found in collaboration with the NCl, Schultz et al., *J. Med. Chem.*, 2909–2019 (1999) and Kunick et al., *Bioorg. Med. Chem. Lett.*, 10, 567–569 (2000). Indenopyrazoles are described in WIPO International Publication Nos. WO 99/17769 and WO 99/54308. Pyrazolo-pyridines are reported in WIPO International Publication No. WO 99/30710. Also known are the fluorene derivatives shown below in Comparison Examples 1 and 2; see also Pan et al., *Chem. & Ind.*, 240–241 (1969), who disclose Comparison Example 2(a) and other 9-oxofluorene oximes:

Comparison Example 1

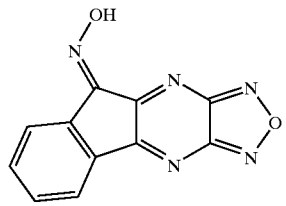

Comparison Example 2

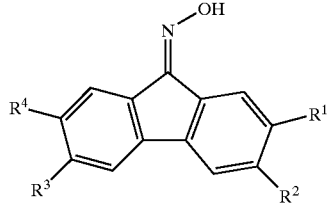

2(a) $R^1 = NH_2$; $R^2 = NO_2$; $R^3$, $R^4 = H$
2(b) $R^1$, $R^2 = NH_2$; $R^3$, $R^4 = H$
2(c) $R^1$, $R^4 = NH_2$; $R^2$, $R^3 = NO_2$

There is still a need, however, for other small-molecule compounds that may be readily synthesized and are potent inhibitors of one or more CDKs or CDK/cyclin complexes. See Gray et al., *Curr. Med. Chem.*, 6, 859–875 (1999) and Sielecki et al., *J. Med. Chem.*, 43, 1–18 (2000). Because CDK4 may serve as a general activator of cell division in most cells, and because complexes of CDK4/cyclin D and CDK2/cyclin E govern the early $G_1$ phase of the cell-cycle, there is a need for effective and specific inhibitors of CDK4 and/or CDK2 for treating one or more types of tumors. Also, the pivotal roles of cyclin E/CDK2 and cyclin B/CDK1 kinases in the $G_1$/S phase and $G_2$/M transitions, respectively offer additional targets for therapeutic intervention in suppressing deregulated cell-cycle progression in cancer.

Another protein kinase, CHK-1, plays an important role as a checkpoint in cell-cycle progression. Checkpoints are control systems that coordinate cell-cycle progression by influencing the formation, activation and subsequent inactivation of the cyclin-dependent kinases. Checkpoints prevent cell-cycle progression at inappropriate times, maintain the metabolic balance of cells while the cell is arrested, and in some instances can induce apoptosis (programmed cell death) when the requirements of the checkpoint have not been met. See, e.g., Chen et al., *Cell*, 100, 681–692 (2000); O'Connor, *Cancer Surveys*, 29, 151–182 (1997); Nurse, *Cell*, 91, 865–867 (1997); Hartwell et al., *Science*, 266, 1821–1828 (1994); and Hartwell et al., *Science*, 246, 629–634 (1989).

One series of checkpoints monitors the integrity of the genome and, upon sensing DNA damage, these "DNA damage checkpoints" block cell-cycle progression in $G_1$ and $G_2$ phases, and slow progression through S phase. O'Connor, *Cancer Surveys*, 29, 151–182 (1997); Hartwell et al., *Science*, 266, 1821–1828 (1994). This action enables DNA repair processes to complete their tasks before replication of the genome and subsequent separation of this genetic material into new daughter cells takes place. Importantly, the most commonly mutated gene in human cancer, the p53 tumor suppressor gene, produces a DNA damage checkpoint protein that blocks cell-cycle progression in $G_1$ phase and/or induces apoptosis (programmed cell death) following DNA damage. Hartwell et al., *Science*, 266, 1821–1828 (1994). The p53 tumor suppressor has also been shown to strengthen the action of a DNA damage checkpoint in $G_2$ phase of the cell-cycle. See, e.g., Bunz et al., *Science*, 28, 1497–1501 (1998); Winters et al., *Oncogene*, 17, 673–684 (1998); Thompson, *Oncogene*, 15, 3025–3035 (1997).

Given the pivotal nature of the p53 tumor suppressor pathway in human cancer, therapeutic interventions that exploit vulnerabilities in p53-defective cancer have been actively sought. One emerging vulnerability lies in the operation of the $G_2$ checkpoint in p53 defective cancer cells. Cancer cells, because they lack $G_1$ checkpoint control, are particularly vulnerable to abrogation of the last remaining barrier protecting them from the cancer killing effects of DNA-damaging agents: the $G_2$ checkpoint. The $G_2$ checkpoint is regulated by a control system that has been conserved from yeast to humans. Important in this conserved system is a kinase, CHK-1, which transduces signals from the DNA-damage sensory complex to inhibit activation of the cyclin B/Cdc2 kinase, which promotes mitotic entry. See, e.g., Peng et al., *Science*, 277, 1501–1505 (1997); Sanchez et al., *Science*, 277, 1497–1501 (1997). Inactivation of CHK-1 has been shown to both abrogate $G_2$ arrest induced by DNA damage inflicted by either anticancer agents or endogenous DNA damage, as well as result in preferential killing of the resulting checkpoint defective cells. See, e.g., Suganuma et al., *Cancer Res.*, 59, 5887–5891 (1999); Nurse, *Cell*, 91, 865–867 (1997); Weinert, *Science*, 277, 1450–1451 (1997); Walworth et al., *Nature*, 363, 368–371 (1993); and Al-Khodairy et al.,*Molec. Biol. Cell* 5, 147–160 (1994).

Selective manipulation of checkpoint control in cancer cells could afford broad utilization in cancer chemotherapeutic and radiotherapy regimens and may, in addition, offer a common hallmark of human cancer "genomic instability" to be exploited as the selective basis for the destruction of cancer cells. A number of factors place CHK-1 as a pivotal target in DNA-damage checkpoint control. The elucidation of inhibitors of this and functionally related kinases such as CDS1/CHK-2, a kinase recently discovered to cooperate with CHK-1 in regulating S phase progression (see Zeng et al., *Nature*, 395, 507–510 (1998); Matsuoka, *Science*, 282, 1893–1897 (1998); Carr, *Science*, 287, 1765–1766 (2000); and Hirao et al., *Science*, 287, 1824–1827 (2000)), could provide valuable new therapeutic entities for the treatment of cancer.

Tyrosine kinases can be of the receptor type (having extracellular, transmembrane and intracellular domains) or the non-receptor type (being wholly intracellular). At least one of the non-receptor protein tyrosine kinases, namely, LCK, is believed to mediate the transduction in T-cells of a signal from the interaction of a cell-surface protein (Cd4) with a cross-linked anti-Cd4 antibody. A more detailed discussion of non-receptor tyrosine kinases is provided in Bolen, *Oncogene*, 8, 2025–2031 (1993), which is incorporated herein by reference.

In addition to their role in cell-cycle control, protein kinases also play a crucial role in angiogenesis, which is the mechanism by which new capillaries are formed from existing vessels. When required, the vascular system has the potential to generate new capillary networks in order to maintain the proper functioning of tissues and organs. In the adult, however, angiogenesis is fairly limited, occurring only in the process of wound healing and neovascularization of the endometrium during menstruation. See Merenmies et al., *Cell Growth & Differentiation*, 8, 3–10 (1997). On the other hand, unwanted angiogenesis is a hallmark of several diseases, such as retinopathies, psoriasis, rheumatoid arthritis, age-related macular degeneneration, and cancer (solid tumors). See Folkman, *Nature Med.*, 1, 27–31 (1995). Protein kinases which have been shown to be involved in the angiogenic process include three members of the growth factor receptor tyrosine kinase family: VEGF-R2 (vascular endothelial growth factor receptor 2, also known as KDR (kinase insert domain receptor) and as FLK-1); FGF-R (fibroblast growth factor receptor); and TEK (also known as Tie-2).

VEGF-R2, which is expressed only on endothelial cells, binds the potent angiogenic growth factor VEGF and mediates the subsequent signal transduction through activation of its intracellular kinase activity. Thus, it is expected that direct inhibition of the kinase activity of VEGF-R2 will result in the reduction of angiogenesis even in the presence of exogenous VEGF (see Strawn et al., *Cancer Research*, 56, 3540–3545 (1996)), as has been shown with mutants of VEGF-R2 which fail to mediate signal transduction. Millauer et al., *Cancer Research*, 56, 1615–1620 (1996). Furthermore, VEGF-R2 appears to have no function in the adult beyond that of mediating the angiogenic activity of VEGF. Therefore, a selective inhibitor of the kinase activity of VEGF-R2 would be expected to exhibit little toxicity.

Similarly, FGF-R binds the angiogenic growth factors aFGF and bFGF and mediates subsequent intracellular signal transduction. Recently, it has been suggested that growth factors such as bFGF may play a critical role in inducing angiogenesis in solid tumors that have reached a certain size. See Yoshiji et al., *Cancer Research*, 57, 3924–3928 (1997). Unlike VEGF-R2, however, FGF-R is expressed in a number of different cell types throughout the body and may or may not play important roles in other normal physiological processes in the adult. Nonetheless, systemic administration of a small molecule inhibitor of the kinase activity of FGF-R has been reported to block bFGF-induced angiogenesis in mice without apparent toxicity. See, e.g., Mohammadi et al., *EMBO Journal*, 17, 5896–5904 (1998).

TEK (also known as Tie-2) is another receptor tyrosine kinase expressed only on endothelial cells which has been shown to play a role in angiogenesis. The binding of the factor angiopoietin-1 results in autophosphorylation of the kinase domain of TEK and results in a signal transduction process which appears to mediate the interaction of endothelial cells with peri-endothelial support cells, thereby facilitating the maturation of newly formed blood vessels. The factor angiopoietin-2, on the other hand, appears to antagonize the action of angiopoietin-1 on TEK and disrupts angiogenesis. See Maisonpierre et al., *Science*, 277, 55–60 (1997).

As a result of the above-described developments, it has been proposed to treat angiogenesis by the use of compounds inhibiting the kinase activity of VEGF-R2, FGF-R, and/or TEK. For example, WIPO International Publication No. WO 97/34876 discloses certain cinnoline derivatives that are inhibitors of VEGF-R2, which may be used for the treatment of disease states associated with abnormal angiogenesis and/or increased vascular permeability such as cancer, diabetes, psoriasis, rheumatoid arthritis, Kaposi's sarcoma, haemangioma, acute and chronic nephropathies, atheroma, arterial restinosis, autoimmune diseases, acute inflammation and ocular diseases with retinal vessel proliferation.

In addition to the protein kinases identified above, many other protein kinases have been considered to be therapeutic targets, and numerous publications disclose inhibitors of kinase activity, as reviewed in the following: McMahon et al., *Oncologist*, 5, 3–10 (2000); Garcia-Echeverria et al., *Med. Res. Rev.*, 20, 28–57 (2000); Holash et al., *Oncogene*, 18, 5356–5362 (1999); Stover et al., *Curr. Opin. Drug Disc. Dev.*, 2, 274–285 (1999); Toledo et al., *Curr Med. Chem.*, 6, 775–805 (1999); Thomas et al., *J. Biol. Chem.*, 274, 36684–36692 (1992); Cohen, *Curr. Op. Chem. Biol.*, 10, 544–549 (1999); Adams et al., *Curr. Opin. Drug Disc. Dev.*, 2, 96–109 (1999); McMahon et al., *Curr. Opin. Drug Disc. Dev.*, 1, 131–146 (1998); and Strawn et al., *Exp. Opin. Invest. Drugs*, 7, 553–573 (1998).

There is still a need, however, for effective inhibitors of protein kinases. Moreover, as would be understood by those skilled in the art, it is desirable for kinase inhibitors to possess both high affinity for the target kinase as well as high selectivity versus other protein kinases.

SUMMARY OF THE INVENTION

Accordingly, an objective of the invention is to discover potent inhibitors of protein kinases. Another objective of the invention is to discover effective kinase inhibitors having a strong and selective affinity for a particular kinase.

These and other objectives of the invention, which will become apparent from the following description, have been achieved by the discovery of the heterocyclic-hydroxyimino-fluorene nuclei compounds, pharmaceutically acceptable prodrugs, pharmaceutically active metabolites, and pharmaceutically acceptable salts thereof (such compounds, prodrugs, metabolites and salts are collectively referred to as "agents") described below, which modulate and/or inhibit the activity of protein kinases. Pharmaceutical compositions containing such agents are useful in treating diseases mediated by kinase activity, such as cancer, as well as other disease states associated with unwanted angiogenesis and/or cellular proliferation, such as diabetic retinopathy, glaucoma, rheumatoid arthritis, restenosis, and psoriasis. Further, the agents have advantageous properties relating to the modulation and/or inhibition of the kinase activity associated with CDK complexes, CHK-1, CDS1, LCK, VEGF-R, and/or FGF-R.

In a general aspect, the invention relates to compounds of the Formula I:

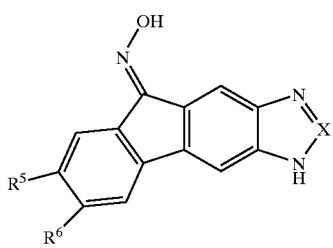

I wherein:
   $R^5$ and $R^6$ are each independently hydrogen, halo, or a substituted or unsubstituted $C_1$–$C_8$ alkyl, $C_1$–$C_8$ alkoxy, aryl, heteroaryl, acyl, thioalkyl, sulfonyl, or sulfoxyl; and
   X is C—Y or N, where Y is hydrogen, halo, $NH_2$, $NO_2$, or a substituted or unsubstituted alkyl, cycloalkyl, heterocycloalkyl, alkoxy, alkenyl, aryl, heteroaryl, aryloxy, alkylamino, dialkylamino, thioalkyl, acyl, sulfonyl, sulfoxide, or thioaryl.

The invention is also directed to pharmaceutically acceptable prodrugs, pharmaceutically active metabolites, and pharmaceutically acceptable salts of the compounds of Formula I and their pharmaceutically active metabolites. Advantageous methods of making the compounds of the Formula I are also described.

In a preferred general embodiment, the invention relates to compounds having Formula I, wherein: $R^5$ and $R^6$ are each independently hydrogen, halo, or a substituted or unsubstituted $C_1$–$C_8$ alkyl; and X is C—Y or N, where Y is hydrogen, halo, $NH_2$, $NO_2$, or a substituted or unsubstituted alkyl or aryl. In another preferred embodiment, the invention relates to compounds having Formula I, wherein: $R^5$ and $R^6$ are each independently hydrogen or halo; X is C—Y or N, where Y is hydrogen, $NH_2$, or $NO_2$.

In another general aspect, the invention relates to compounds of the Formula II:

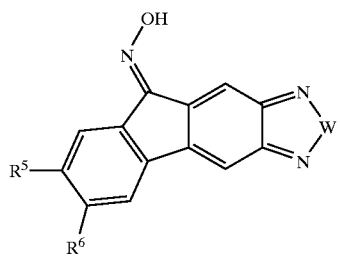

II wherein:
   $R^5$ and $R^6$ are each independently hydrogen, halo, or a substituted or unsubstituted $C_1$–$C_8$ alkyl, $C_1$–$C_8$ alkoxy, aryl, heteroaryl, acyl, thioalkyl, sulfonyl, or sulfoxyl; and
   W is O or S.

The invention is also directed to pharmaceutically acceptable prodrugs, pharmaceutically active metabolites, and pharmaceutically acceptable salts of the compounds of Formula II and their pharmaceutically active metabolites. Advantageous methods of making the compounds of the Formula II are also described.

In a preferred general embodiment, the invention relates to compounds having Formula II, wherein: $R^5$ and $R^6$ are each independently hydrogen, halo, or a substituted or unsubstituted $C_1$–$C_8$ alkyl; and W is O or S. In another preferred embodiment, the invention relates to compounds having Formula II, wherein: $R^5$ and $R^6$ are each independently hydrogen or halo; and W is O or S.

The invention also relates to a method of modulating and/or inhibiting the kinase activity of a CDK complex, VEGF-R, FGF-R, CHK-1, CDS1, and/or LCK by administering a compound of Formula I or II or a pharmaceutically acceptable prodrug, pharmaceutically active metabolite, or pharmaceutically acceptable salt of such compound or metabolite thereof. Preferably, compounds of the present invention have selective kinase activity—i.e., they possess significant activity against one specific kinase while possessing less or minimal activity against a different kinase.

The invention also relates to pharmaceutical compositions, each comprising an effective amount of an agent selected from compounds of Formula I and II and pharmaceutically active metabolites, pharmaceutically acceptable prodrugs, and pharmaceutically acceptable salts of such compounds and metabolites, and a pharmaceutically acceptable carrier or vehicle for such agent. The invention further provides methods of treating cancer as well as other disease states associated with unwanted angiogenesis and/or cellular proliferation, comprising administering effective amounts of one or more such agents to a patient in need of such treatment.

DETAILED DESCRIPTION OF THE INVENTION AND PREFERRED EMBODIMENTS

The inventive compounds of Formula I and II are useful for modulating the activity of protein kinases. More particularly, the compounds are useful as anti-angiogenesis agents and as agents for modulating and/or inhibiting the activity of protein kinases, thus providing treatments for cancer or other diseases associated with cellular proliferation mediated by protein kinases.

The terms "comprising" and "including" are used herein in their open, non-limiting sense.

The term "alkyl" as used herein refers to straight- and branched-chain alkyl groups having one to twelve carbon atoms. Exemplary alkyl groups include methyl (Me), ethyl, n-propyl, isopropyl, butyl, isobutyl, sec-butyl, tert-butyl (tBu), pentyl, isopentyl, tert-pentyl, hexyl, isohexyl, and the like. The term "lower alkyl" designates an alkyl having from 1 to 8 carbon atoms (a $C_{1-8}$-alkyl). Exemplary substituted alkyls include fluoromethyl, difluoromethyl, trifluoromethyl, 2-fluoroethyl, 3-fluoropropyl, hydroxymethyl, 2-hydroxyethyl, 3-hydroxypropyl, and the like.

The term "alkenyl" refers to straight- and branched-chain alkenyl groups having from two to twelve carbon atoms. Illustrative alkenyl groups include prop-2-enyl, but-2-enyl, but-3-enyl, 2-methylprop-2-enyl, hex-2-enyl, and the like.

The term "cycloalkyl" refers to saturated carbocycles having from three to twelve carbon atoms, including bicyclic and tricyclic cycloalkyl structures. Exemplary cycloalkyls include cyclopropyl, cyclobutyl, cyclopentyl, cyclohexyl, cycloheptyl, and the like.

A "heterocycloalkyl" group refers to a monocyclic radical containing carbon atoms, preferably 4 or 5 ring carbon atoms, and at least one heteroatom selected from nitrogen, oxygen and sulfur, and having no unsaturation.

The terms "aryl" (Ar) and "heteroaryl" refer to monocyclic and polycyclic unsaturated or aromatic ring structures, with "aryl" referring to those that are carbocycles and "heteroaryl" referring to those that are heterocycles. Examples of aromatic ring structures include phenyl, naphthyl, 1,2,3,4-tetrahydronaphthyl, furyl, thienyl, pyrrolyl, pyridyl, pyridinyl, pyrazolyl, imidazolyl, pyrazinyl, pyridazinyl, 1,2,3-triazinyl, 1,2,4-oxadiazolyl, 1,3,4-oxadiazolyl, 1-H-tetrazol-5-yl, indolyl, quinolinyl, benzofuranyl, benzothiophenyl (thianaphthenyl), and the like. Such moieties may be optionally substituted by one or more suitable substituents, for example, a substituent selected from a halogen (F, Cl, Br or I); lower alkyl; OH; $NO_2$; CN; $CO_2H$; O-lower alkyl; aryl; aryl-lower alkyl; $CO_2CH_3$; $CONH_2$; $OCH_2CONH_2$; $NH_2$; $SO_2NH_2$; $OCHF_2$; $CF_3$; $OCF_3$; and the like. Such moieties may also be optionally substituted by a fused-ring structure or bridge, for example $OCH_2$—O.

The term "alkoxy" refers to the radical —O-alkyl. Illustrative examples include methoxy, ethoxy, propoxy, and the like.

The term "aryloxy" respresents —O-aryl, wherein aryl is defined above.

The term "halogen" represents chlorine, fluorine, bromine or iodine. The term "halo" represents chloro, fluoro, bromo or iodo.

The term "alkylamino" represents —NHR where R is an alkyl group as defined above.

The term "dialkylamino" represents —$NHR_aR_b$ where $R_aR_b$ are each independently an alkyl group as defined above.

The term "thioalkyl" refers to the radical —SR where R is an alkyl group as defined above.

The term "acyl" represents —C(O)H, —C(O)OH, —C(O)R, —C(O)OR, —C(O)$NH_2$, —C(O)NHR, and —C(O)$NHR_aR_b$, where R and $R_aR_b$ are as defined above.

The term "thioaryl" refers to the radical —SAr where Ar is an aryl group as defined above.

The term "sulfonyl" represents the radical —$SO_2R$ or —$SO_2Ar$, where R is an alkyl group and Ar is an aryl group as defined above.

The term "sulfoxyl" represents the radical —SOR or —SOAr, where R is an alkyl group and Ar is an aryl group as defined above.

As indicated, the various moieties or functional groups for variables in the formulae may be optionally substituted by one or more suitable substituents. Exemplary substituents include a halogen (F, Cl, Br, or I), lower alkyl, —OH, —$NO_2$, —CN, —$CO_2H$, —O-lower alkyl, -aryl, -aryl-lower alkyl, —$CO_2CH_3$, —$CONH_2$, —$OCH_2CONH_2$, —$NH_2$, —$SO_2NH_2$, haloalkyl (e.g., —$CF_3$, —$CH_2CF_3$), —O-haloalkyl (e.g., —$OCF_3$, —$OCHF_2$), and the like.

The compounds of the invention may exhibit the phenomenon of tautomerism. While Formula I and II cannot expressly depict all possible tautomeric forms, it is to be understood that Formula I and II are intended to represent any tautomeric form of the depicted compound and are not to be limited merely to a specific compound form depicted by the formula drawings. For example, Formula I may tautomerize to the following structure:

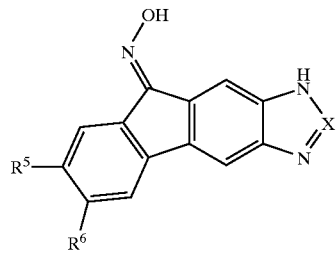

It is also understood that a compound of Formula I or II may exist as an "E" or "Z" configurational isomer, or a mixture of E and Z isomers. For example, an E isomer exists when the hydroxy (—OH) substituent of the oxime is on the opposite side of the heterocyclic-portion of a compound depicted in Formula I, wherein a Z isomer exists when the hydroxy (—OH) substituent is on the same side as the heterocyclic-portion of a compound, as expressly depicted in Formula I. A mixture of E and Z isomers is indicated by a wavy bond between the nitrogen atom and hydroxy substituent, as expressly depicted in Examples A–F. It is therefore to be understood that Formula I and II are intended to represent any configurational form of the depicted compound and is not to be limited merely to a specific compound form depicted by the formula drawings.

Some of the inventive compounds may exist as single stereoisomers (i.e., essentially free of other stereoisomers), racemates, and/or mixtures of enantiomers and/or diastereomers. All such single stereoisomers, racemates and mixtures thereof are intended to be within the scope of the present invention. Preferably, the inventive compounds that are optically active are used in optically pure form.

As generally understood by those skilled in the art, an optically pure compound having one chiral center (i.e., one asymmetric carbon atom) is one that consists essentially of one of the two possible enantiomers (i.e., is enantiomerically pure), and an optically pure compound having more than one chiral center is one that is both diastereomerically pure and enantiomerically pure. Preferably, the compounds of the present invention are used in a form that is at least 90% optically pure, that is, a form that contains at least 90% of a single isomer (80% enantiomeric excess ("e.e.") or diastereomeric excess ("d.e.")), more preferably at least 95% (90% e.e. or d.e.), even more preferably at least 97.5% (95% e.e. or d.e.), and most preferably at least 99% (98% e.e. or d.e.).

Additionally, the formulas are intended to cover solvated as sell as unsolvated forms of the identified structures. For example, Formula I includes compounds of the indicated structure in both hydrated and non-hydrated forms. Other examples of solvates include the structures in combination with isopropanol, ethanol, methanol, DMSO, ethyl acetate, acetic acid, or ethanolamine.

In addition to compounds of Formulas I and II, the invention includes pharmaceutically acceptable prodrugs, pharmaceutically active metabolites, and pharmaceutically acceptable salts of such compounds and metabolites.

"A pharmaceutically acceptable prodrug" is a compound that may be converted under physiological conditions or by solvolysis to the specified compound or to a pharmaceutically acceptable salt of such compound.

"A pharmaceutically active metabolite" is intended to mean a pharmacologically active product produced through metabolism in the body of a specified compound or salt thereof.

Prodrugs and active metabolites of a compound may be identified using routine techniques known in the art. See, e.g., Bertolini et al., *J. Med. Chem.*, 40, 2011–2016 (1997); Shan, et al., *J. Pharm. Sci.*, 86 (7), 765–767; Bagshawe, *Drug Dev. Res.*, 34, 220–230 (1995); Bodor, *Advances in Drug Res.*, 13, 224–331 (1984); Bundgaard, *Design of Prodrugs* (Elsevier Press 1985); and Larsen, *Design and Application of Prodrugs,* Drug Design and Development (Krogsgaard-Larsen et al., eds., Harwood Academic Publishers, 1991).

"A pharmaceutically acceptable salt" is intended to mean a salt that retains the biological effectiveness of the free acids and bases of the specified compound and that is not biologically or otherwise undesirable. A compound of the invention may possess a sufficiently acidic, a sufficiently basic, or both functional groups, and accordingly react with any of a number of inorganic or organic bases, and inorganic and organic acids, to form a pharmaceutically acceptable salt. Exemplary pharmaceutically acceptable salts include those salts prepared by reaction of the compounds of the present invention with a mineral or organic acid or an inorganic base, such as salts including sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4 -dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methane-sulfonates, propanesulfonates, naphthalene-1-sulfonates, naphthalene-2-sulfonates, and mandelates.

If the inventive compound is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the inventive compound is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

In the case of agents that are solids, it is understood by those skilled in the art that the inventive compounds and salts may exist in different crystal or polymorphic forms, all of which are intended to be within the scope of the present invention and specified formulas.

Therapeutically effective amounts of the agents of the invention may be used to treat diseases mediated by modulation or regulation of protein kinases. An "effective amount" is intended to mean that amount of an agent that, when administered to a mammal in need of such treatment, is sufficient to effect treatment for a disease mediated by the activity of one or more protein kinases, such as tryosine kinases. Thus, e.g., a therapeutically effective amount of a compound of the Formula I, salt, active metabolite or prodrug thereof is a quantity sufficient to modulate, regulate, or inhibit the activity of one or more protein kinases such that a disease condition which is mediated by that activity is reduced or alleviated.

The amount of a given agent that will correspond to such an amount will vary depending upon factors such as the particular compound, disease condition and its severity, the identity (e.g., weight) of the mammal in need of treatment, but can nevertheless be routinely determined by one skilled in the art. "Treating" is intended to mean at least the mitigation of a disease condition in a mammal, such as a human, that is affected, at least in part, by the activity of one or more protein kinases, such as tyrosine kinases, and includes: preventing the disease condition from occurring in a mammal, particularly when the mammal is found to be predisposed to having the disease condition but has not yet been diagnosed as having it; modulating and/or inhibiting the disease condition; and/or alleviating the disease condition.

The affinity of the compounds of the invention for a receptor may be enhanced by providing multiple copies of the ligand in close proximity, preferably using a scaffolding provided by a carrier moiety. It has been shown that provision of such multiple valence compounds with optimal spacing between the moieties dramatically improves binding to a receptor. See, e.g., Lee et al., *Biochemistry*, 23, 4255 (1984). The multivalency and spacing can be controlled by selection of a suitable carrier moiety or linker units. Such moieties include molecular supports which contain a multiplicity of functional groups that can be reacted with functional groups associated with the compounds of the invention. Of course, a variety of carriers can be used, including proteins such as BSA (bovine serum albumin) or HSA (human serum albumin), various peptides including, for example, pentapeptides, decapeptides, and pentadecapeptides, and the like. The peptides or proteins can contain the desired number of amino acid residues having free amino groups in their side chains; however, other functional groups, such as sulfhydryl groups or hydroxyl groups, can also be used to obtain stable linkages.

Agents that potently regulate, modulate, or inhibit the protein kinase activity associated with receptors CDK complexes, VEGF, FGF, CHK-1, CDS1, and LCK, among others, and which inhibit angiogenesis and/or cellular profileration are preferred. The present invention is further directed to methods of modulating or inhibiting protein kinase activity, for example in mammalian tissue, by administering an inventive agent. The activity of the inventive agents as modulators of protein kinase activity, such as the activity of kinases, may be measured by any of the methods available to those skilled in the art, including in vivo and/or in vitro assays. Examples of suitable assays for activity measurements include those described in WIPO International Publication No. WO 99/21845; Parast et al., *Biochemistry*, 37, 16788–16801 (1998); Jeffrey et al., *Nature,* 376, 313–320 (1995); WIPO International Publication No. WO 97/34876; and WIPO International Publication No. WO 96/14843. These properties may be assessed, for example, by using one or more of the biological testing procedures set out in the examples below.

The active agents of the invention may be formulated into pharmaceutical compositions as described below. Pharmaceutical compositions of this invention comprise an effective modulating, regulating, or inhibiting amount of a compound of Formula I or Formula II and an inert, pharmaceutically acceptable carrier or diluent. In one embodiment of the pharmaceutical compositions, efficacious levels of the inventive agents are provided so as to provide therapeutic benefits involving modulation of protein kinases. By "efficacious levels" is meant levels in which the effects of protein kinases are, at a minimum, regulated. These compositions are prepared in unit-dosage form appropriate for the mode of administration, e.g., parenteral or oral administration.

An inventive agent can be administered in conventional dosage form prepared by combining a therapeutically effective amount of an agent (e.g., a compound of Formula I) as an active ingredient with appropriate pharmaceutical carriers or diluents according to conventional procedures. These procedures may involve mixing, granulating and compressing or dissolving the ingredients as appropriate to the desired preparation.

The pharmaceutical carrier employed may be either a solid or liquid. Exemplary of solid carriers are lactose, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time-delay or time-release material known in the art, such as glyceryl monostearate or glyceryl distearate alone or with a wax, ethylcellulose, hydroxypropylmethylcellulose, methylmethacrylate and the like.

A variety of pharmaceutical forms can be employed. Thus, if a solid carrier is used, the preparation can be tableted, placed in a hard gelatin capsule in powder or pellet form or in the form of a troche or lozenge. The amount of solid carrier may vary, but generally will be from about 25 mg to about 1 g. If a liquid carrier is used, the preparation will be in the form of syrup, emulsion, soft gelatin capsule, sterile injectable solution or suspension in an ampoule or vial or non-aqueous liquid suspension.

To obtain a stable water-soluble dose form, a pharmaceutically acceptable salt of an inventive agent is dissolved in an aqueous solution of an organic or inorganic acid, such as 0.3 M solution of succinic acid or citric acid. If a soluble salt form is not available, the agent may be dissolved in a suitable cosolvent or combinations of cosolvents. Examples of suitable cosolvents include, but are not limited to, alcohol, propylene glycol, polyethylene glycol 300, polysorbate 80, gylcerin and the like in concentrations ranging from 0–60% of the total volume. In an exemplary embodiment, a compound of Formula I is dissolved in DMSO and diluted with water. The composition may also be in the form of a solution of a salt form of the active ingredient in an appropriate aqueous vehicle such as water or isotonic saline or dextrose solution.

It will be appreciated that the actual dosages of the agents used in the compositions of this invention will vary according to the particular complex being used, the particular composition formulated, the mode of administration and the particular site, host and disease being treated. Optimal dosages for a given set of conditions can be ascertained by those skilled in the art using conventional dosage-determination tests in view of the experimental data for an agent. For oral administration, an exemplary daily dose generally employed is from about 0.001 to about 1000 mg/kg of body weight, with courses of treatment repeated at appropriate intervals. Administration of prodrugs are typically dosed at weight levels which are chemically equivalent to the weight levels of the fully active form.

The compositions of the invention may be manufactured in manners generally known for preparing pharmaceutical compositions, e.g., using conventional techniques such as mixing, dissolving, granulating, dragee-making, levigating, emulsifying, encapsulating, entrapping or lyophilizing. Pharmaceutical compositions may be formulated in a conventional manner using one or more physiologically acceptable carriers, which may be selected from excipients and auxiliaries that facilitate processing of the active compounds into preparations which can be used pharmaceutically.

Proper formulation is dependent upon the route of administration chosen. For injection, the agents of the invention may be formulated into aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained using a solid excipient in admixture with the active ingredient (agent), optionally grinding the resulting mixture, and processing the mixture of granules after adding suitable auxiliaries, if desired, to obtain tablets or dragee cores. Suitable excipients include: fillers such as sugars, including lactose, sucrose, mannitol, or sorbitol; and cellulose preparations, for example, maize starch, wheat starch, rice starch, potato starch, gelatin, gum, methyl cellulose, hydroxypropylmethyl-cellulose, sodium carboxymethylcellulose, or polyvinylpyrrolidone (PVP). If desired, disintegrating agents may be added, such as crosslinked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, polyvinyl pyrrolidone, Carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active agents.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with fillers such as lactose, binders such as starches, and/or lubricants such as talc or magnesium stearate, and, optionally, stabilizers. In soft capsules, the active agents may be dissolved or suspended in suitable liquids, such as fatty oils, liquid paraffin, or liquid polyethylene glycols. In addition, stabilizers may be added. All formulations for oral administration should be in dosages suitable for such administration. For buccal administration, the compositions may take the form of tablets or lozenges formulated in conventional manner.

For administration intranasally or by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of gelatin for use in an inhaler or insufflator and the like may be formulated containing a powder mix of the compound and a suitable powder base such as lactose or starch.

The compounds may be formulated for parenteral administration by injection, e.g., by bolus injection or continuous infusion. Formulations for injection may be presented in unit-dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active agents may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

For administration to the eye, a compound of Formula I or Formula II is delivered in a pharmaceutically acceptable ophthalmic vehicle such that the compound is maintained in contact with the ocular surface for a sufficient time period to allow the compound to penetrate the corneal and internal regions of the eye, including, for example, the anterior chamber, posterior chamber, vitreous body, aqueous humor, vitreous humor, cornea, iris/cilary, lens, choroid/retina and scelera. The pharmaceutically acceptable ophthalmic vehicle may be an ointment, vegetable oil, or an encapsulating material. A compound of the invention may also be injected directly into the vitreous and aqueous humor.

Alternatively, the active ingredient may be in powder form for constitution with a suitable vehicle, e.g., sterile pyrogen-free water, before use. The compounds may also be formulated in rectal compositions such as suppositories or retention enemas, e.g, containing conventional suppository bases such as cocoa butter or other glycerides.

In addition to the formulations described above, the compounds may also be formulated as a depot preparation. Such long-acting formulations may be administered by implantation (for example, subcutaneously or intramuscularly) or by intramuscular injection. Thus, for example, the compounds may be formulated with suitable polymeric or hydrophobic materials (for example, as an emulsion in an acceptable oil) or ion-exchange resins, or as sparingly soluble derivatives, for example, as a sparingly soluble salt.

An examplary pharmaceutical carrier for hydrophobic compounds is a cosolvent system comprising benzyl alcohol, a nonpolar surfactant, a water-miscible organic polymer, and an aqueous phase. The cosolvent system may be a VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) contains VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may be substituted for dextrose.

Alternatively, other delivery systems for hydrophobic pharmaceutical compounds may be employed. Liposomes and emulsions are known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid- or gel-phase carriers or excipients. Examples of such carriers or excipients include calcium carbonate, calcium phosphate, sugars, starches, cellulose derivatives, gelatin, and polymers such as polyethylene glycols.

Some of the compounds of the invention may be provided as salts with pharmaceutically compatible counter ions. Pharmaceutically compatible salts may be formed with many acids, including hydrochloric, sulfuric, acetic, lactic, tartaric, malic, succinic, etc. Salts tend to be more soluble in aqueous or other protonic solvents than are the corresponding free-base forms.

The inventive agents may be prepared using the reaction routes and synthesis schemes as described below, employing the general techniques known in the art using starting materials that are readily available. The preparation of preferred compounds of the present invention is described in detail in the following examples, but the artisan will recognize that the chemical reactions described may be readily adapted to prepare a number of other protein kinase inhibitors of the invention. For example, the synthesis of non-exemplified compounds according to the invention may be successfully performed by modifications apparent to those skilled in the art, e.g., by appropriately protecting interfering groups, by changing to other suitable reagents known in the art, or by making routine modifications of reaction conditions. Alternatively, other reactions disclosed herein or generally known in the art will be recognized as having applicability for preparing other compounds of the invention.

EXAMPLES

In the examples described below, unless otherwise indicated all temperatures are set forth in degrees Celsius and all parts and percentages are by weight. Reagents were pur chased from commercial suppliers such as Aldrich Chemical Company or Lancaster Synthesis Ltd. and were used without further purification unless otherwise indicated. Tetrahydrofuran (THF) and N,N-dimethylforamide (DMF) were purchased from Aldrich in Sure Seal bottles and used as received. All solvents were purified using standard methods known to those skilled in the art, unless otherwise indicated.

The reactions set forth below were done generally under a positive pressure of argon at an ambient temperature (unless otherwise stated) in anhydrous solvents, and the reaction flasks were fitted with rubber septa for the introduction of substrates and reagents via syringe. Glassware was oven dried and/or heat dried. Analytical thin layer chromatography (TLC) was performed on glass-backed silica gel 60 F 254 plates from Analtech (0.25 mm), eluted with the appropriate solvent ratios (v/v), and are denoted where appropriate. The reactions were assayed by TLC and terminated as judged by the consumption of starting material.

Visualization of the TLC plates was done with iodine vapor, ultraviolet illumination, 2% $Ce(NH_4)_4(SO_4)_4$ in 20% aqueous sulfuric acid, or p-anisaldehyde spray reagent, and activated with heat where appropriate. Work-ups were typically done by doubling the reaction volume with the reaction solvent or extraction solvent and then washing with the indicated aqueous solutions using 25% by volume of the extraction volume unless otherwise indicated. Product solutions were dried over anhydrous $Na_2SO_4$ and/or $Mg_2SO_4$ prior to filtration and evaporation of the solvents under reduced pressure on a rotary evaporator and noted as solvents removed in vacuo. Flash column chromatography (Still et al., *J. Org. Chem.*, 43, 2923 (1978)) was done using Merck silica gel (47–61 μm) with a silica gel crude material ratio of about 20:1 to 50:1, unless otherwise stated. Hydrogenolysis was done at the pressure indicated in the examples or at ambient pressure.

$^1$H-NMR spectra were recorded on a Bruker or Varian instrument operating at 300 MHz and $^{13}$C-NMR spectra were recorded operating at 75 MHz. NMR spectra were obtained as $CDCl_3$ solutions (reported in ppm), using chloroform as the reference standard (7.27 ppm and 77.00 ppm) or $CD_{3OD}$ (3.4 and 4.8 ppm and 49.3 ppm), or internally tetramethylsilane (0.00 ppm) when appropriate. Other NMR solvents were used as needed. When peak multiplicities are reported, the following abbreviations are used: s(singlet), d(doublet), t(triplet), q(quartet), m(multiplet), br(broadened), dd (doublet of doublets), dt(doublet of triplets). Coupling constants, when given, are reported in Hertz(Hz).

Infrared (IR) spectra were recorded on a Perkin-Elmer FT-IR Spectrometer as neat oils, as KBr pellets, or as $CDCl_3$ solutions, and when given are reported in wave numbers ($cm^{-1}$). The mass spectra were obtained using LSIMS, FAB, or electrospray. All melting points (mp) are uncorrected.

Example A

9(E/Z)-Hydroxyimino-3H-fluoreno[2,3-d]imidazole

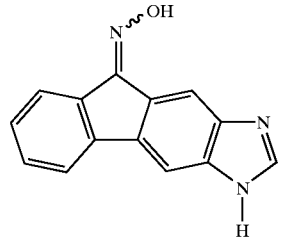

(1) 2,3-Diamino-fluoren-9-one, which has structural formula

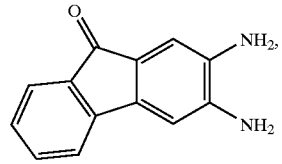

was first prepared as follows. To a solution of $SnCl_2.2H_2O$ (749 mg, 3.32 mmol) in a mixture of concentrated HCl (1.2 mL) and glacial acetic acid (2 mL) was added 2-amino-3-nitro-fluoren-9-one (200 mg, 0.83 mmol, obtained from Aldrich). The resulting suspension was refluxed for 3 h and allowed to cool to ambient temperature. The solid was filtered off and rinsed with concentrated HCl and $H_2O$ until the filtrate became violet. The filtrate was basified to pH 9 with 1N NaOH. The precipitate was filtered off, rinsed with $H_2O$, and dried under vacuum to furnish a brown powder, 140 mg (80% yield), which matched that previously described by Eckert et al., *Journal für Praktische Chemie*, 118, 263–281 (1928), and was used without further purification. FTIR (KBr) 3419, 3331, 1735, 1672, 1619, 1584, 1448, 1390 $cm^{-1}$; $^1$H NMR ($CD_3OD$) δ7.26–7.39 (m, 4H), 7.12 (t, 2H, J=7.2 Hz), 6.92 (s, 2H), 6.79 (s, 2H).

(2) To prepare 2,3-diamino-9(E/Z)-hydroxyimino-fluorene, which has structural formula

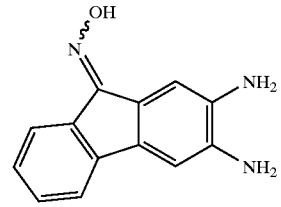

a procedure from Pan et al., *Chem. & Ind.*, 240–241 (1969) was followed. To a solution of 2,3-diamino-fluoren-9-one (from A(1); 200 mg, 0.95 mmol) in DMSO (1.5 mL) was added a solution of hydroxylamine hydrochloride (72 mg, 1.0 mmol) in $H_2O$ (250 μL). The resultant solution was heated at 70° C. for a half hour, allowed to cool to ambient temperature, and diluted with $H_2O$ (5 mL). The resultant solid was filtered off, rinsed with $H_2O$ and benzene, and dried under vacuum to furnish a brown powder, 190 mg (89% yield), mp 145–47° C. FTIR (KBr) 3201, 3036, 2848, 1619, 1596, 1449, 1372, 1313 $cm^{-1}$; $^1$H NMR (DMSO-$d_6$) δ8.24 (d, 1H, J=7.5 Hz), 7.82 (d, 1H, J=3.1 Hz), 7.45 (d, 1H, J=6.9 Hz), 6.94–7.44 (m, 8H); MS (FAB) [M+Na$^+$]: 248;

HRMS (FAB) [MH⁺] Calc'd 226.0980, Found, 226.0987; Anal. Calc'd for $C_{13}H_{11}N_3O\cdot0.63$ DMSO: C, 62.40; H, 5.43; N, 15.31. Found: C, 62.15; H, 5.04; N, 15.52.

(3) To prepare the title compound, a suspension of 2,3-diamino-9(E/Z)-hydroxyimino-fluorene (from A(2); 100 mg, 0.44 mmol) in a mixture of triethyl orthoformate (0.5 mL) and glacial acetic acid (0.5 mL) was refluxed for 3 h, allowed to cool to ambient temperature, and filtered. The filtrate was basified to pH 8 with 1N NaOH, and the resultant solid was filtered off, rinsed with $H_2O$, dried under vacuum, and recrystallized from EtOH/$CHCl_3$ to furnish a brown powder, 85 mg (82% yield), mp 262° C. FTIR (KBr) 3375, 3065, 2974, 2256, 1694, 1595, 1450, 1225 cm⁻¹; ¹H NMR ($CD_3OD$) δ8.18 (d, 1H, J=13.1 Hz), 7.94 (s, 1H), 7.88 (d, 2H, J=8.1 Hz), 7.65–7.81 (m, 2H), 7.20–7.48 (m, 3H); HRMS (FAB) Calc'd for $C_{14}H_{10}N_3O$ (MH⁺): 236.0824. Found: 236.0834; Anal. Calc'd for $C_{14}H_9N_3O\cdot0.3$ $CHCl_3\cdot0.5$ EtOH: C, 62.49; H, 4.22; N, 14.29. Found: C, 62.26; H, 4.17; N, 14.21.

Example B

2-Amino-9(E/Z)-hydroxyimino-3H-fluoreno[2,3-d]imidazole

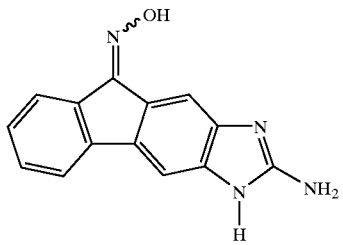

To a suspension of 2,3-diamino-9(E/Z)-hydroxyiminofluorene (from Example A(2); 100 mg, 0.44 mmol) in $H_2O$ (1.5 mL) was added BrCN (47 mg, 0.44 mmol). The resultant mixture stirred at ambient temperature for 24 h and was filtered. The filtrate was basified to pH 8 with 1N NaOH. The resultant solid was filtered off, rinsed with $H_2O$ and cold $CH_2Cl_2$, and dried under vacuum to furnish a brown powder, 100 mg (91% yield), mp 240–42° C. FTIR (KBr) 3470, 3344, 1588, 1497, 1385, 1319, 1248 cm⁻¹; ¹H NMR (DMSO-$d_6$) δ8.12 (d, 1H, J=7.2 Hz), 8.10 (s, 1H), 7.10–7.70 (m, 6H), 6.38 (s, 1H), 6.25 (s, 1H); HRMS (FAB) Calc'd for $C_{14}H_{11}N_4O$ [MH⁺]: 251.0933. Found: 251.0945; Anal. Calc'd for $C_{14}H_{10}N_4O\cdot0.12$ $CH_2Cl_2$: C, 65.45; H, 3.97; N, 21.65. Found: C, 65.35; H, 4.23; N, 21.25.

Example C

9(E/Z)-Hydroxyimino-3H-fluoreno[2,3-d]-1,2,3-triazole

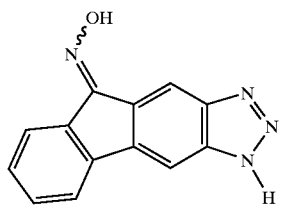

To a suspension of 2,3-diamino-9(E/Z)-hydroxyiminofluorene (from Example A(2); 100 mg, 0.44 mmol) in $H_2O$ (1.4 mL) at 0° C. was added glacial acetic acid (51 μL, 0.88 mmol) and a solution of $NaNO_2$ (33 mg, 0.48 mmol) in $H_2O$ (0.6 mL). The resultant mixture was heated at 70° C. for a half-hour, allowed to cool to ambient temperature, and filtered. The filtrate was basified to pH 9 with 58% aqueous $NH_4OH$. The precipitate was filtered off, rinsed with $H_2O$ and cold $CHCl_3$, and dried under vacuum to furnish a brown powder, 100 mg (96% yield), mp 222–24° C. FTIR (KBr) 3193, 3062, 2870, 1626, 1443, 1381, 1194 cm⁻¹; ¹H NMR (DMSO-$d_6$) δ8.38 (d, 1H, J=7.8 Hz), 8.22 (s, 1H), 7.98–8.18 (m, 2H), 7.70 (d, 1H, J=7.5 Hz), 7.30–7.58 (m, 3H); (HRMS (FAB) Calc'd for $C_{13}H_9N_4O$ [MH⁺]: 237.0776. Found: 237.0772; Anal. Calc'd for $C_{13}H_8N_4O\cdot0.24$ $CHCl_3$: C, 60.14; H, 3.14; N, 21.15. Found: C, 60.14; H, 3.49; N, 20.84.

Example D

9(E/Z)-Hydroxyimino-7-iodo-3H-fluoreno[2,3-d]-1,2,3-triazole

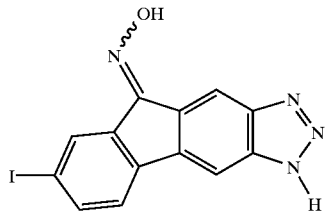

(1) 2-Amino-7-iodo-9H-fluorene, which has the structural formula

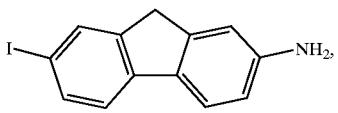

was first prepared in a manner analogous to 2,3-diaminofluoren-9-one for Example A(1), except that 7-iodo-2-nitrofluorene (see Marhevka et al., *J. Med. Chem.*, 28, 18–24 (1985); also obtained from Aldrich) was used instead of 2-amino-3-nitro-fluoren-9-one to provide a white powder in 91% yield, which was used without further purification. ¹H NMR (DMSO-$d_6$) δ7.94 (d, 2H, J=8.1 Hz), 7.72 (dd, 2H, J=10.3, 8.1 Hz), 7.45 (s, 1H), 7.62 (d, 1H, J=8.1 Hz), 3.98 (s, 2H).

(2) 2-Acetamido-7-iodo-9H-fluorene, which has structural formula

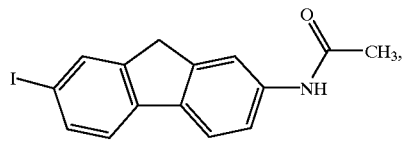

was prepared next. A suspension of 2-amino-7-iodo-9H-fluorene (1.50 g, 4.88 mmol) in glacial acetic acid at 80° C. was treated with acetic anhydride (3.23 mL, 34.2 mmol) dropwise over 5 min. The resultant mixture was heated at 90° C. for 2 h and then allowed to cool to ambient temperature. The resultant solid was collected by filtration, rinsed with $H_2O$, dried under vacuum to furnish a white powder, 1.3 g (76% yield), which was used without further purification. ¹H NMR (DMSO-$d_6$) δ10.02 (s, 1H), 7.88 (s, 2H), 7.78 (d, 1H, J=8.4 Hz), 7.68 (d, 1H, J=8.1 Hz), 7.60 (d, 1H, J=8.1 Hz), 7.48 (d, 1H, J=8.4 Hz), 3.82 (s, 2H), 2.02 (s, 3H).

(3) 2-Acetamido-7-iodo-3-nitro-9H-fluorene, which has structural formula

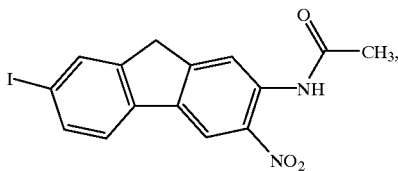

was prepared next. To a suspension of 2-acetamido-7-iodo-9H-fluorene (2.37 g, 6.79 mmol) in glacial acetic acid (245 mL) at 95° C. was added dropwise over 3 min a solution of concentrated HNO$_3$ (730 μL, 11.5 mmol) in glacial acetic acid (5 mL). The resultant mixture was heated to 100° C. for 30 min, allowed to cool to ambient temperature, and poured onto crushed ice. The resultant solid was filtered off, rinsed with H$_2$O, and dried under vacuum to furnish a yellow solid, 1.8 g (67% yield), which was used without further purification. $^1$H NMR (DMSO-d$_6$) δ8.58 (s, 1H), 7.98 (s, 1H), 7.84 (t, 2H, J=8.1 Hz), 7.75 (d, 1H, J=8.1 Hz), 4.02 (s, 2H), 2.02 (s, 3H); Anal. Calc'd for C$_{15}$H$_9$N$_2$O$_4$.0.2 H$_2$O: C, 43.76; H, 2.30; N, 6.80. Found: C, 43.41; H, 2.30; N, 6.56.

(4) 2-Acetamido-7-iodo-3-nitro-fluoren-9-one, which has structural formula

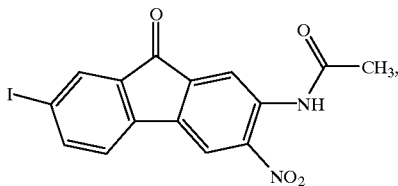

was prepared next. To a suspension of 2-acetamido-7-iodo-3-nitro-9H-fluorene (1.5 g, 3.81 mmol) in glacial acetic acid (150 mL) was added potassium dichromate (1.68 g, 5.71 mmol). The resulting mixture was heated to reflux for 3 h. The mixture was allowed to cool to ambient temperature and poured onto H$_2$O. The resultant solid was filtered off, rinsed with H$_2$O, and recrystallized from boiling THF to furnish a pink powder, 850 mg (55% yield), which was used without further purification. $^1$H NMR (DMSO-d6) δ10.42 (s, 1H), 8.42 (s, 1H), 8.04 (d, 1H, J=7.8 Hz), 7.92 (s, 1H), 7.78 (dd, 2H, J=7.8, 7.2 Hz), 2.02 (s, 3H).

(5) 2-Amino-7-iodo-3-nitro-fluoren-9-one, which has structural formula

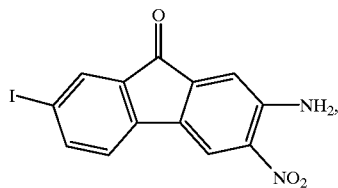

was prepared next. To a suspension of N-(7-iodo-3-nitro-9-oxo-9H-fluoren-2-yl)-acetamide (450 mg, 1.10 mmol) in a mixture of n-butanol and ethanol (40 ml, 1:1) was added 50% H$_2$SO$_4$ (5 ml). The resulting mixture was heated to reflux for 3 h. The mixture was allowed to cool to ambient temperature and diluted with H$_2$O. The resulting solid was filtered off, rinsed with H$_2$O, and dried under vacuum to furnish a brown solid, 400 mg (99% yield), which was used without further purification. $^1$H NMR (DMSO-d$_6$) δ8.38 (s, 1H), 8.08 (s, 2H), 7.96 (d, 1H, J=7.8 Hz), 7.88 (s, 1H), 7.72 (d, 1H, J=8.1 Hz), 7.36 (s, 1H); MS (ESI) [MH$^+$]: 367.

(6) 2,3-Diamino-7-iodo-fluoren-9-one, which has structural formula

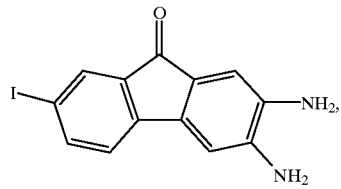

was prepared in a manner analogous to 2,3-diamino-fluoren-9-one for Example A(1), except that 2-amino-7-iodo-3-nitro-fluoren-9-one was used in place of 2-amino-3-nitro-fluoren-9-one, to provide a brown powder in 75% yield, which was used without further purification. $^1$H NMR (DMSO-d$_6$) δ7.92 (dd, 1H, J=7.8, 1.6 Hz), 7.76 (d, 1H, J=1.6 Hz), 7.48 (s, 1H), 7.44 (d, 1H, J=7.8 Hz), 7.09 (s, 1H); MS (ESI) [MH$^+$]: 337; Anal. Calc'd for C$_{15}$H$_9$N$_2$O$_4$.1 HCl: C, 41.91; H, 2.71; N, 7.52. Found: C, 42.09; H, 2.67; N, 7.34.

(7) 7-Iodo-9-oxo-fluoreno[2,3-d]-1,2,3-triazole, which has the structural formula

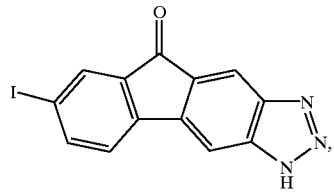

was prepared in a manner analogous to 7-iodo-9-oxo-3H-fluoreno[2,3-d]-1,2,3-triazole in Example C, except that 2,3-diamino-7-iodo-fluoren-9-one was used in place of 2,3-diamino-9(E/Z)-hydroxyimino-fluorene, to provide a brownish-yellow powder in 93% yield, which was used without further purification. $^1$H NMR (DMSO-d$_6$) δ8.22 (bs, 1H), 8.03 (d, 1H, J=8.1 Hz), 7.90 (d, 1H, J=8.1 Hz) 7.83 (d, 1H, J=6.9 Hz), 7.76 (s, 1H), 7.64 (dd, 1H, J=7.8, 6.5 Hz); MS (ESI) [MH$^+$]: 348; Anal. Calc'd for C$_{13}$H$_6$N$_3$O.0.6H$_2$O: C, 43.62; H, 2.03; N, 11.74. Found: C, 43.90; H, 2.05; N, 11.36.

(8) The title compound was prepared in a manner like that described for Example A(2) except that 7-iodo-9-oxo-3H-fluoreno[2,3-d]-1,2,3-triazole was used in place of 2,3-diamino-fluoren-9-one, to provide a brown powder in 65% yield, mp 275–77° C.; FTIR (KBr) 3194, 3061, 2912, 1626, 1588, 1439, 1377, 1194 cm$^{-1}$; $^1$H NMR (CD$_3$OD) δ8.80 (bs, 1H), 8.17 (bs, 1H), 8.10 (s, 1H), 7.86 (d, 1H, J=7.8 Hz), 7.62–7.78 (m, 2H); HRMS (FAB) Calc'd for C$_{13}$H$_8$IN$_4$O [MH$^+$]: 362.9743. Found: 362.9755; Anal. Calc'd for C$_{13}$H$_7$IN$_4$O.0.5 CHCl$_3$: C, 39.35; H, 2.08; N, 13.02. Found: C, 39.61; H, 2.48; N, 12.72.

Example E

7-Iodo-2-oxa-9(E/Z)-oximino-1,3-diaza-cyclopenta[b]fluorene

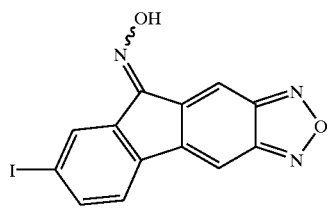

(1) 7-Iodo-2-oxa-1,3-diaza-cyclopenta[b]fluoren9-one, which has the structural formula

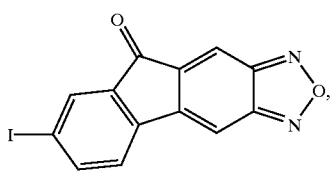

was prepared from 2-amino-7-iodo-3-nitro-fluoren-9-one (Example D(5)) according to a multistep procedure of Perera et al., *J. Chem. Soc.* (C), 1348–1354 (1971). Treatment with sodium nitrite and aqueous hydrochloric acid generates a diazonium derivative, which is displaced by sodium azide and decomposed in hot acetic acid to the title heterocycle.

The title compound is prepared in a manner similar to that described for Example A(1) from 7-iodo-2-oxa-1,3-diaza-cyclopenta[b]fluoren-9-one.

Example F

7-Iodo-9(E/Z)-oximino-1,3-diaza-2-thia-cyclopenta[b]fluorene

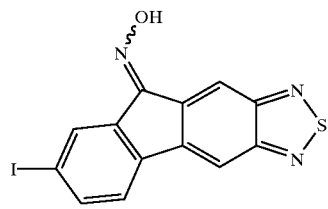

(1) 7-iodo-1,3-diaza-2-thia-cyclopenta[b]fluoren-9-one, which has the structural formula

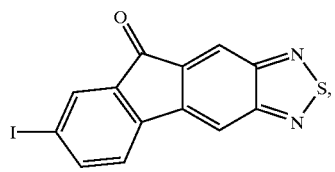

is prepared from 2,3-diamino-7-iodo-fluoren-9-one (Example D(6)) according to a procedure described by Matsumoto et al., *Chem. Pharm. Bull.*, 47, 971–979 (1999) (referencing Khaletski et al., *Doklady Akad. Nauk S.S.S.R.*, 106, 88–91, *Chem. Abstr.*, 50, 13885c (1956)). The reaction with thionyl chloride and triethylamine in benzene at reflux provides the title heterocycle.

The title compound is prepared in a manner similar to that described for Example A(1) from 7-iodo-1,3-diaza-2-thia-cyclopenta[b]fluoren-9-one.

Biological Testing; Enzyme Assays

The stimulation of cell proliferation by growth factors such as VEGF and others is dependent upon their induction of autophosphorylation of each of their respective receptor's tyrosine kinases. Therefore, the ability of a protein kinase inhibitor to block cellular proliferation induced by these growth factors is directly correlated with its ability to block receptor autophosphorylation. To measure the protein kinase inhibition activity of the compounds, the following constructs were devised.

VEGF-R2 Construct for Assay: A construct (VEGF-R2Δ50) of the cytosolic domain of human vascular endothelial growth factor receptor 2 (VEGF-R2) lacking the 50 central residues of the 68 residues of the kinase insert domain was expressed in a baculovirus/insect cell system. Of the 1356 residues of full-length VEGF-R2, VEGF-R2Δ50 contains residues 806–939 and 990–1171, and also one point mutation (E990V) within the kinase insert domain relative to wild-type VEGF-R2. See McTigue et al., *Structure*, 7, 319–330 (1999); U.S. patent application Ser. No. 09/390,326, filed Sep. 7, 1999. Autophosphorylation of the purified construct was performed by incubation of the enzyme at a concentration of 4 $\mu$M in the presence of 3 mM ATP and 40 mM $MgCl_2$ in 100 mM Hepes, pH 7.5, containing 5% glycerol and 5 mM DTT, at 4° C. for 2 h. After autophosphorylation, this construct has been shown to possess catalytic activity essentially equivalent to the wild-type autophosphorylated kinase domain construct. See Parast et al., *Biochemistry*, 37, 16788–16801 (1998).

CHK-1 Constructs for Assay: C-terminally His-tagged full-length human CHK-1 (FL-CHK-1) was expressed using the baculovirus/insect cell system. It contains 6 histidine residues (6×His-tag) at the C-terminus of the 476 amino acid human CHK-1. The protein was purified by conventional chromatographic techniques.

CHK-1 KH289 contains residues 1–289 of human CHK-1 including the kinase domain. It contains 6 histidine residues (6×His-tag) at the C-terminus of residue 289. The protein was expressed in a baculovirus/insect cell system and purified by conventional chromatographic techniques.

CDK2/Cyclin A Construct for Assay: CDK2 was purified using published methodology (Rosenblatt et al., *J. Mol. Biol.*, 230, 1317–1319 (1993)) from insect cells that had been infected with a baculovirus expression vector. Cyclin A was purified from *E. coli* cells expressing full-length recombinant cyclin A, and a truncated cyclin A construct was generated by limited proteolysis and purified as described previously (Jeffrey et al., *Nature*, 376, 313–320 (1995)).

CDK4/Cyclin D Construct for Assay: A complex of human CDK4 and cyclin D3, or a complex of cyclin D1 and a fusion protein of human CDK4 and glutathione-S-transferase (GST-CDK4), was purified using traditional biochemical chromatographic techniques from insect cells that had been co-infected with the corresponding baculovirus expression vectors.

CDS1 Construct for Assay: CDS1 CE4 contains residues 209–502 including the kinase domain of human CDS1/CHK-2 (GenBank accession number AFO86904, Matsuoka et al., *Science*, 282, 1893–97 (1998)). It contains the amino acid sequence: MGSSHHHHHHSSGLVPRSHM at the N-terminus of residue 209. (The first M is not present in the expressed protein due to post-translational processing of the N-terminus.) The protein was expressed in *E. coli* and purified by conventional chromatographic techniques.

VEGF-R2 Assay

Coupled Spectrophotometric (FLVK-P) Assay

The production of ADP from ATP that accompanies phosphoryl transfer was coupled to oxidation of NADH using phosphoenolpyruvate (PEP) and a system having pyruvate kinase (PK) and lactic dehydrogenase (LDH). The oxidation of NADH was monitored by following the decrease of absorbance at 340 nm ($e_{340}$=6.22 cm$^{-1}$ mM$^{-1}$) using a Beckman DU 650 spectrophotometer. Assay conditions for phosphorylated VEGF-R2Δ50 (indicated as FLVK-P in the tables below) were the following: 1 mM PEP; 250 μM NADH; 50 units of LDH/mL; 20 units of PK/mL; 5 mM DTT; 5.1 mM poly($E_4Y_1$); 1 mM ATP; and 25 mM $MgCl_2$ in 200 mM Hepes, pH 7.5. Assay conditions for unphosphorylated VEGF-R2Δ50 (indicated as FLVK in the tables) were the following: 1 mM PEP; 250 ,M NADH; 50 units of LDH/mL; 20 units of PK/mL; 5 mM DTT; 20 mM poly($E_4Y_1$); 3 mM ATP; and 60 mM $MgCl_2$ and 2 mM $MnCl_2$ in 200 mM Hepes, pH 7.5. Assays were initiated with 5 to 40 nM of enzyme. $K_i$ values were determined by measuring enzyme activity in the presence of varying concentrations of test compounds. The data were analyzed using Enzyme Kinetic and Kaleidagraph software.

ELISA Assay

Formation of phosphogastrin was monitored using biotinylated gastrin peptide (1–17) as substrate. Biotinylated phosphogastrin was immobilized using streptavidin coated 96-well microtiter plates followed by detection using anti-phosphotyrosine-antibody conjugated to horseradish peroxidase. The activity of horseradish peroxidase was monitored using 2,2'-azinobis-[3-ethylbenzthiazoline sulfonate] diammonium salt (ABTS). Typical assay solutions contained: 2 μM biotinylated gastrin peptide; 5 mM DTT; 20 μM ATP; 26 mM $MgCl_2$; and 2 mM $MnCl_2$ in 200 mM Hepes, pH 7.5. The assay was initiated with 0.8 nM of phosphorylated VEGF-R2Δ50. Horseradish peroxidase activity was assayed using ABTS, 10 mM. The horseradish peroxidase reaction was quenched by addition of acid ($H_2SO_4$), followed by absorbance reading at 405 nm. $K_i$ values were determined by measuring enzyme activity in the presence of varying concentrations of test compounds. The data were analyzed using Enzyme Kinetic and Kaleidagraph software.

CHK-1 Assay

The production of ADP from ATP that accompanies phosphoryl transfer to the synthetic substrate peptide Syntide-2 (PLARTLSVAGLPGKK) was coupled to oxidation of NADH using phosphoenolpyruvate (PEP) through the actions of pyruvate kinase (PK) and lactic dehydrogenase (LDH). The oxidation of NADH was monitored by following the decrease of absorbance at 340 nm ($\epsilon 340$=6.22 cm$^{-1}$ mM$^{-1}$) using a HP8452 spectrophotometer. Typical reaction solutions contained: 4 mM PEP; 0.15 mM NADH; 28 units of LDH/ml; 16 units of PK/ml; 3 mM DTT; 0.125 mM Syntide2Σ; 0.15 mM ATP; 25 mM $MgCl_2$ in 50 mM TRIS, pH 7.5; and 400 mM NaCl. Assays were initiated with 10 nM of CHK-1 KH289. $K_i$ values were determined by measuring initial enzyme activity in the presence of varying concentrations of test compounds. The data were analyzed using Enzyme Kinetic and Kaleidagraph software.

CDS 1 Assay

The CDS 1 assay was prepared under identical conditions to that of the CHK-1 assay, except with the use of 10 nM of CDS1.

CDK2/Cyclin A and CDK4/Cyclin D Assays

Cyclin-dependent kinase activity was measured by quantifying the enzyme-catalyzed, time-dependent incorporation of radioactive phosphate from [$^{32}$P]ATP into a recombinant fragment of the retinoblastoma protein. Unless noted otherwise, assays were performed in 96-well plates in a total volume of 50 μL, in the presence of 10 mM HEPES (N-[2-hydroxyethyl]piperazine-N'-[2-ethanesulfonic acid]) (pH 7.4), 10 mM $MgCl_2$, 25 μM adenosine triphosphate (ATP), 1 mg/mL ovalbumin, 5 μg/mL leupeptin, 1 mM dithiothreitol, 10 mM β-glycerophosphate, 0.1 mM sodium vanadate, 1 mM sodium fluoride, 2.5 mM ethylene glycol-bis(β-aminoethyl ether)-N,N,N'N'-tetraacetic acid (EGTA), 2% (v/v) dimethylsulfoxide, and 0.03–0.2 μCi [$^{32}$P]ATP. The substrate (0.3–0.5 μg) was purified recombinant retinoblastoma protein fragment (Rb) (residues 386–928 of the native retinoblastoma protein; 62.3 kDa, containing the majority of the phosphorylation sites found in the native 1 06kDa protein, as well as a tag of six histidine residues for ease of purification). Reactions were initiated with CDK2 (150 nM CDK2/Cyclin A complex) or CDK4 (50 nM CDK4/Cyclin D3 complex), incubated at 30° C., and terminated after 20 minutes by the addition of ethylenediaminetetraacetic acid (EDTA) to 250 mM. The phosphorylated substrate was then captured on a nitrocellulose membrane using a 96-well filtration manifold, and unincorporated radioactivity was removed by repeated washing with 0.85% phosphoric acid. Radioactivity was quantified by exposing the dried nitrocellulose membranes to a phosphorimager. Apparent $K_i$ values were measured by assaying enzyme activity in the presence of different compound concentrations and subtracting the background radioactivity measured in the absence of enzyme. The kinetic parameters (kcat, Km for ATP) were measured for each enzyme under the usual assay conditions by determining the dependence of initial rates on ATP concentration. The data were fit to an equation for competitive inhibition using Kaleidagraph (Synergy Software), or were fit to an equation for competitive tight-binding inhibition using the software KineTic (BioKin, Ltd.). The specific activity of CDK4 was the same whether complexed to full-length cyclin D3 or the truncated Cyclin D3 construct; both complexes also yielded very similar $K_i$ values for selected inhibitors.

Inhibition of Cell Growth: Assessment of Anti-proliferation with U2-OS, SAOS2, HCT116 Cancer Cell Lines Inhibition of cell growth was measured using the tetrazolium salt assay, which is based on the ability of viable cells to reduce 3-(4,5-dimethylthiazol-2-yl)-2,5-[2H]-diphenyltetrazolium bromide (MTT) to formazan (Mossman, *J. Immunological Methods*, 65, 55–58 (1983)). The water-insoluble purple formazan product was then detected spectrophotometrically. The HCT 116, U2-OS, and SAOS 2 cell lines were each grown in 96-well plates, respectively. Cells were plated in the appropriate medium at a volume of 135 μL/well in McCoy's 5A Medium. Plates were incubated for 4 h before addition of inhibitor compounds.

Different concentrations of inhibitor compounds were added in 0.5% (v/v) dimethylsulfoxide (μL/well), and cells were incubated at 37° C. (5% $CO_2$) for four to six days (depending on cell type). At the end of the incubation, MTT was added to a final concentration of 0.2 mg/mL, and cells were incubated for 4 h more at 37° C. After centrifugation of the plates and removal of medium, the absorbance of the formazan (solubilized in dimethylsulfoxide) was measured at 540 nm. The concentration of inhibitor compound causing 50% inhibition of growth was determined from the linear portion of a semi-log plot of inhibitor concentration versus percentage inhibition. All results were compared to control cells treated only with 0.5% (v/v) dimethylsulfoxide.

The results of the testing of the compounds using various assays are summarized in the table below, where a notation of "% @" indicates the percent inhibition at the stated concentration.

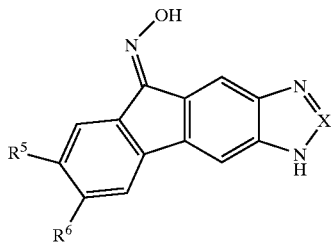

| Ex. | CDK4/D3 Ki (μM) | CDK2/A Ki (μM) | VEGF/ FLVK-P Ki (μM) | CHK-1 KH289 Ki (μM) | HCT 116 IC$_{50}$ (μM) | CDS1 Ki (μM) | U2-OS IC$_{50}$ (μM) | SAOS2 IC$_{50}$ (μM) |
|---|---|---|---|---|---|---|---|---|
| A | 2.36 | | 1.33 | 3.6 | | | | |
| B | 0.79 | | 1.9 | 5.8 | | | | |
| C | 0.213 | 0.680 | 1.47 | 0.571 | 10.4 | | 18.0 | 11.0 |
| D | 1.2 | | | 0.166 | | 0.021 | | |
| Comparison Ex. 1 | 2.1 | | 15.9 | 26.6 | | 15 | | |
| Comparison Ex. 2(a) | 1.79 | | 15.5 | 14% @ 10 μM | | | | |
| Comparison Ex. 2(b) | 3.21 | | 0.923 | 8.1 | | 0.604 | | |
| Comparison Ex. 2(c) | 3.62 | | | 33% @ 25 μM | | 37 | | |

The exemplary compounds described above may be formulated into pharmaceutical compositions according to the following general examples.

Example 1

Parenteral Composition

To prepare a parenteral pharmaceutical composition suitable for administration by injection, 100 mg of a water-soluble salt of a compound of the Formula I or Formula II is dissolved in DMSO and then mixed with 10 mL of 0.9% sterile saline. The mixture is incorporated into a dosage unit form suitable for administration by injection.

Example 2

Oral Composition

To prepare a pharmaceutical composition for oral delivery, 100 mg of a compound of Formula I or Formula II is mixed with 750 mg of lactose. The mixture is incorporated into an oral dosage unit for, such as a hard gelatin capsule, which is suitable for oral administration.

Example 3

Intraocular Composition

To prepare a sustained-release pharmaceutical composition for intraocular delivery, a compound of Formula I or Formula II is suspended in a neutral, isotonic solution of hyaluronic acid (1.5% conc.) in phosphate buffer (pH 7.4) to form a 1% suspension.

It is to be understood that the foregoing description is exemplary and explanatory in nature, and is intended to illustrate the invention and its preferred -embodiments. Through routine experimentation, the artisan will recognize apparent modifications and variations that may be made without departing from the spirit of the invention. Thus, the invention is intended to be defined not by the above description, but by the following claims and their equivalents.

What is claimed is:

1. A compound of the Formula I:

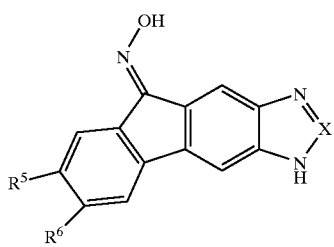

wherein:

$R^5$ and $R^6$ are each independently hydrogen, halo, or a substituted or unsubstituted $C_1$-$C_8$ alkyl, $C_1$-$C_8$ alkoxy, aryl, heteroaryl, acyl, thioalkyl, sulfonyl, or sulfoxyl; and X is C—Y or N, where Y is hydrogen, halo, $NH_2$, $NO_2$, or a substituted or unsubstituted alkyl, cycloalkyl, heterocycloalkyl, alkoxy, alkenyl, aryl, heteroaryl, aryloxy, alkylamino, dialkylamino, thioalkyl, acyl, sulfonyl, sulfoxide, or thioaryl;

or a pharmaceutically acceptable prodrug of said compound, or pharmaceutically acceptable salt of said compound or metabolite.

2. A compound, prodrug, or salt according to claim 1, wherein:

$R^5$ and $R^6$ are each independently hydrogen, halo, or a substituted or unsubstituted $C_1$-$C_8$ alkyl; and X is C—Y or N, where Y is hydrogen, halo, $NH_2$, $NO_2$, or a substituted or unsubstituted alkyl or aryl.

3. A compound, prodrug, or salt according to claim 1, wherein:

$R^5$ and $R^6$ are each independently hydrogen or halo; and X is C—Y or N, where Y is hydrogen, $NH_2$, or $NO_2$.

4. A compound of the Formula II:

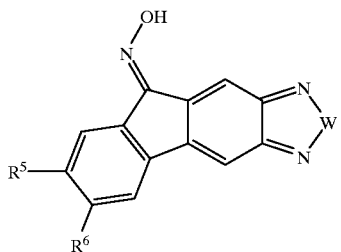

wherein:
   $R^5$ and $R^6$ are each independently hydrogen, halo, or a substituted or unsubstituted $C_1$–$C_8$ alkyl, $C_1$–$C_8$ alkoxy, aryl, heteroaryl, acyl, thioalkyl, sulfonyl, or sulfoxyl; and
   W is O or S;
   or a pharmaceutically acceptable prodrug of said compound, or pharmaceutically acceptable salt of said compound or metabolite.

5. A compound, prodrug, or salt according to claim 4, wherein:
   $R^5$ and $R^6$ are each independently hydrogen, halo, or a substituted or unsubstituted $C_1$–$C_8$ alkyl; and W is O or S.

6. A compound, prodrug, or salt according to claim 4, wherein:
   $R^5$ and $R^6$ are each independently hydrogen or halo; and W is O or S.

7. A method of modulating or inhibiting the activity of a protein kinase receptor for the treatment of a disease condition in mammals, mediated by protein kinase activity, comprising administering to a mammal in need thereof a therapeutically effective amount of a compound, pharmaceutically acceptable prodrug, or pharmaceutically acceptable salt as defined in claim 1.

8. A method according to claim 7, wherein the disease condition is tumor growth, cell proliferation, or angiogenesis.

9. A method of according to claim 7, wherein the protein kinase receptor is a CDK complex, VEGF-R, FGF-1, CHK-1, CDS1, or LCK.

10. A method of modulating or inhibiting the activity of a protein kinase receptor for the treatment of a disease condition in mammals mediated by protein kinase activity, comprising administering to a mammal in need thereof a therapeutically effective amount of a compound, pharmaceutically acceptable prodrug, or pharmaceutically acceptable salt as defined in claim 4.

11. A method according to claim 10, wherein the disease condition is tumor growth, cell proliferation, or angiogenesis.

12. A method according to claim 10, wherein the protein kinase receptor is a CDK complex, VEGF-R, FGF-1, CHK-1, CDS1, or LCK.

* * * * *